US006462052B1

(12) United States Patent
Duvert et al.

(10) Patent No.: US 6,462,052 B1
(45) Date of Patent: Oct. 8, 2002

(54) SYNERGISTIC FUNGICIDE AND/OR BACTERICIDE COMPOSITION

(75) Inventors: Patrice Duvert, Lyons; André Gillet, Bron, both of (FR)

(73) Assignee: Rhone-Poulenc Agro (FR)

( * ) Notice: Subject to any disclaimer, the term of this patent is extended or adjusted under 35 U.S.C. 154(b) by 0 days.

(21) Appl. No.: 09/674,128

(22) PCT Filed: Apr. 12, 1999

(86) PCT No.: PCT/FR99/00845

§ 371 (c)(1),
(2), (4) Date: Nov. 13, 2000

(87) PCT Pub. No.: WO99/55160

PCT Pub. Date: Nov. 4, 1999

(30) Foreign Application Priority Data

Apr. 27, 1998 (FR) ............................................ 98 05583

(51) Int. Cl.$^7$ ........................ A01N 43/54; A01N 37/30; A01N 37/52
(52) U.S. Cl. ........................ 514/275; 514/554; 514/634
(58) Field of Search ................................ 514/275, 634, 514/554

(56) References Cited

FOREIGN PATENT DOCUMENTS

GB 2267644 A 12/1992

OTHER PUBLICATIONS

Tomlin, The Pesticide Manual 11$^{th}$ ed. (1997), pp. 319–321, 451,452,784,785,1068 and 1069.*
Chemical Abstracts, vol. 122, No. 9, Feb. 27, 1995, Columbus, Ohio, US: abstract No. 99313, Maeno, Shinichiro et al: "Synergistic microbicides containing pyrimidine an diguanidine derivatives" XP0022090819.
"The pesticide manual" 1994, British Crop Protection Council XP002090821 10$^{TH}$ Edition.

* cited by examiner

Primary Examiner—Allen J. Robinson
(74) Attorney, Agent, or Firm—Ostrolenk, Faber, Gerb & Soffen, LLP

(57) ABSTRACT

The invention concerns a synergistic fungicide and/or bactericide composition comprising dodine and a derivative of the anilino-pyrimidine family. The invention also concerns a preventive or curative method for fighting against phytopathogenic fungi and/or bacteria using such a composition.

15 Claims, No Drawings

1

SYNERGISTIC FUNGICIDE AND/OR BACTERICIDE COMPOSITION this application is a 371 of PCT/FR99/00845, filed Sep. 12, 1999.

The present invention relates to a synergistic fungicidal and/or bactericidal composition comprising dodine and a compound of the anilino-pyrimidine family, and to a method of using this composition for the curative or preventative protection of crops against fungal attack.

It is always desirable to improve the range of activity and efficacy of such fungicidally active compounds, or to make them more potent by combining them with other molecules in order to obtain an improved product or else to prevent the appearance of fungal strains which are resistant.

Equally, it is very desirable to have available fungicidal products which have an improved duration of action so that the number of plant protection treatments required for good control of the parasites can be spaced out over the course of time.

In any case, it is particularly advantageous to be able to reduce the quantity of chemical products sprayed in the environment while guaranteeing effective protection of the crops against fungal attack.

It has now been found that one (or more) of the above aims can be achieved by the fungicidal and/or bactericidal composition according to the present invention.

The present invention primarily therefore relates to a synergistic fungicidal and/or bactericidal composition comprising, as compound A, dodine, which is also known as dodecylguanidine monoacetate, and at least one fungicidal compound B selected from the group comprising a compound of the anilino-pyrimidine family, that is to say B is chosen from the group comprising cyprodinil, pyrimethanil or mepanipyrim.

The fungicidal and/or bactericidal composition according to the invention advantageously comprises the components A and B in a weight ratio A/B of between 1/26 and 160/1, preferably between 1/4 and 60/1, especially advantageously in a ratio of between 3/8 and 9/1.

Naturally, this fungicidal and/or bactericidal composition can contain a single compound B or more than one such compound, for example, 1, 2 or 3 compounds B, depending on the intended use.

Amongst the more particularly preferred meanings of the above-defined compound B, pyrimethanil is especially preferred. Quite unexpectedly, the composition according to the invention improves in a remarkable manner the activity of active materials taken separately for a number of fungi which are particularly harmful to crops, such as, in particular, grapevine or the potato family. This improvement manifests itself especially by a reduced dosage of each of the constituents, which is particularly advantageous for the user and the environment. The fungicidal and/or bactericidal product (mixture) thus exhibits synergistic properties which are borne out by applying the method defined by Limpel L. E., P. H. Schuldt and D. Lammont, 1962, Proc. NEWCC 16:48–53, using the following formula, also called Colby formula:

$$E = X + Y - X \cdot Y / 100$$

in which:

E is the expected percentage of inhibition of the growth of the fungus by a mixture of the two fungicides A and B at defined doses, respectively equal to a and b;

X is the observed percentage of inhibition by the fungicide and/or bactericide A at the dose a, Y is the observed percentage of inhibition by the fungicide and/or bactericide B at the dose b. When the observed percentage of inhibition for the mixture is greater than E, there is synergism.

When component B is pyrimethanil, the ratio A/B is preferably between 1/4 and 60/1, this ratio especially advantageously being between 3/8 and 9/1, this ratio most preferably being 3/1 for all of the crops under consideration.

The structures which correspond to the common names of the active materials A and B are given in at least one of the 2 following works:

"The pesticide manual", edited by Clive TOMLIN, and published by the British Crop Protection Council, 11th Edition, 1997 (pages 451, 1068, 319 and 784);

The "Index phytosanitaire 1998", edited by the Association de Coordination Technique Agricole, 34th Edition.

The fungicidal and/or bactericidal composition according to the invention comprises, as active material, a compound A and at least one compound B as a mixture with solid or liquid agriculturally acceptable carriers and/or surfactants which are also agriculturally acceptable. Substances which can be used in particular are the usual inert carriers and the usual surfactants. These compositions extend not only to compositions which are ready to be applied to the crop to be treated by means of a suitable device, such as a sprayer, but also to concentrated commercial compositions which must be diluted before being applied to the crop. By active material there is to be understood the combination of at least one compound A with at least one compound B.

These compositions can also contain any type of other ingredients such as, for example, protective colloids, adhesives, thickeners, thixotropes, penetrants, stabilizers, sequestering agents and the like. More generally, the compounds A and B can be combined with all solid or liquid additives which are conventionally used in the art of formulation.

Generally speaking, the compositions according to the invention usually contain from 0.05 to 95% (by weight) of active material, one or more liquid or solid carriers and, if appropriate, one or more surfactants.

The term "carrier" is to be understood as meaning in the present text a natural or synthetic organic or mineral material with which the active material is combined to facilitate its application to the aerial parts of the plant. This carrier is thus generally inert and must be agriculturally acceptable, especially by the treated plant. The carrier may be solid (clays, natural or synthetic silicates, silica, resins, waxes, solid fertilizers and the like) or liquid (water, alcohols, especially butanol, and the like).

The surfactant may be an ionic or nonionic emulsifier, dispersant or wetter, or a mixture of such surfactants. By way of example there may be mentioned salts of polyacrylic acids, of lignosulphonic acids, of phenolsulphonic acids or of naphthalenesulphonic acids, polycondensates of ethylene oxide and fatty alcohols or fatty acids or fatty amines, substituted phenols (especially alkylphenols or arylphenols), salts of sulphosuccinic esters, taurine derivatives (especially alkyl taurates), phosphoric esters of alcohols or of polyoxyethylated phenols, esters of fatty acids and polyols, and derivatives of the above compounds which have a sulphate, sulphonate and phosphate function. The presence of at least one surfactant is generally indispensable when the active material and/or the inert carrier are not soluble in water and when the application vehicle is water.

The compositions according to the invention for use in agriculture can therefore contain the active material within very wide limits of from 0.05% to 95% (by weight). Their surfactant content is advantageously between 5% and 40% by weight. Unless otherwise specified, the percentages given in the present description including the claims are by weight.

These compositions according to the invention, themselves, come in a wide variety of solid or liquid forms.

As solid forms of compositions there may be mentioned powders for dusting (whose active material content may be as high as 100%) and granules, especially those obtained by extrusion, by compacting, by impregnating a granulated carrier, by granulation of a powder (the active material content in these granules being between 0.5 and 80% in the last-mentioned cases), tablets or effervescent tablets.

The fungicidal and/or bactericidal composition according to the invention may also be used in the form of powders for dusting; a composition comprising 50 g of active material and 950 g of talc may also be used; a composition comprising 20 g of active material, 10 g of finely divided silica and 970 g of talc may also be used; these constituents are mixed and ground, and the mixture is applied by dusting.

As liquid forms of compositions, or forms intended to give liquid compositions upon application, there may be mentioned solutions, in particular water-soluble concentrates, emulsions, concentrated suspensions, aerosols, wettable powders (or sprayable powders), pastes, and gels.

Concentrated suspensions which can be applied by spraying are prepared in such a way that a stable fluid product is obtained which does not settle, and they usually contain 10 to 75% of active material, 0.5 to 15% of surfactants, 0.1 to 10% of thixotropes, 0 to 10% of suitable additives such as antifoams, corrosion inhibitors, stabilizers, penetrants and adhesives, and, as carrier, water or an organic liquid in which the active material is sparingly, or not, soluble: certain organic solid materials or mineral salts may be dissolved in the carrier to help prevent settling, or as antifreeze agents for the water.

By way of example there is now given a composition of a concentrated suspension:

| Example SC 1: | |
|---|---|
| active material | 500 g |
| polyethoxylated tristyrylphenol phosphate | 50 g |
| polyethoxylated alkylphenol | 50 g |
| sodium polycarboxylate | 20 g |
| ethylene glycol | 50 g |
| organopolysiloxane oil (antifoam) | 1 g |
| polysaccharide | 1.5 g |
| water | 316.5 g |

Wettable powders (or sprayable powders) are usually prepared in such a way that they contain 20 to 95% of active material; they usually contain, in addition to the solid carrier, 0 to 30% of a wetter, 3 to 20% of a dispersant, and, if necessary, 0.1 to 10% of one or more stabilizers and/or other additives, such as penetrants, adhesives, anticaking agents, colorants and the like.

To obtain sprayable powders, or wettable powders, the active materials are mixed intimately with the additives in suitable mixers and the mixtures are ground in mills or other suitable grinders. This gives sprayable powders with advantageous wetting and suspending properties; they can be suspended in water to give any desired concentration, and these suspensions are very advantageously suitable for foliar application to the plants, in particular.

Instead of wettable powders, pastes may be made. The conditions and modes of making and using these pastes are similar to those for wettable powders or sprayable powders.

By way of example there are now given various compositions of wettable powders (or sprayable powders):

| Example WP 1: | |
|---|---|
| active material | 50% |
| ethoxylated fatty alcohol (wetter) | 2.5% |
| ethoxylated phenylethylphenol (dispersant) | 5% |
| chalk (inert carrier) | 42.5% |
| Example WP 2: | |
| active material | 10% |
| branched synthetic C13-oxoalcohol ethoxylated with 8 to 10 ethylene oxide units (wetter) | 0.75% |
| neutral calcium lignosulphonate (dispersant) | 12% |
| calcium carbonate (inert filler) | to 100% |
| Example WP 3: This wettable powder contains the same ingredients as in the preceding example, but in the following proportions: | |
| active material | 75% |
| wetter | 1.50% |
| dispersant | 8% |
| calcium carbonate (inert filler) | to 100% |
| Example WP 4: | |
| active material | 90% |
| ethoxylated fatty alcohol (wetter) | 4% |
| ethoxylated phenylethylphenol (dispersant) | 6% |
| Example WP 5: | |
| active material | 50% |
| mixture of anionic and nonionic surfactants (wetter) | 2.5% |
| sodium lignosulphonate (dispersant) | 5% |
| kaolin type clay (inert carrier) | 42.5% |

The aqueous dispersions and emulsions, for example the compositions obtained by diluting a wettable powder or an emulsifiable concentrate according to the invention with the aid of water, come within the general scope of the present invention. The emulsions may be of the water-in-oil type or the oil-in-water type and they can have a thick consistency, such as that of a "mayonnaise".

The fungicidal compositions according to the invention may be formulated in the form of water-dispersible granules, which equally come within the scope of the invention.

These dispersible granules, whose apparent density is generally between approximately 0.3 and 0.6, have a particle size of generally between approximately 150 and 2000, preferably between 300 and 1500, microns.

The active material content of these granules is generally between approximately 1% and 90%, preferably between 25% and 90%.

The remainder of these granules is essentially composed of a solid filler and, if appropriate, surface-active adjuvants which impart, to the granules, properties of dispersibility in water. These granules can essentially belong to two different types, depending on whether their filler is water-soluble or not. When the filler is soluble in water, it may be mineral or, preferably, organic. Outstanding results were obtained with urea. An insoluble filler is preferably mineral, such as, for example, kaolin or bentonite. It is advantageously accompanied by surfactants (in a proportion of 2 to 20% by weight of the granules) of which more than half is composed of, for example, at least one essentially anionic dispersant, such as an alkali metal or alkaline earth metal polynaphthalenesulphonate, or an alkali metal or alkaline earth metal lignosulphonate, the remainder being composed of nonionic or anionic wetters, such as an alkali metal or alkaline earth metal alkylnaphthalenesulphonate.

In addition, other adjuvants such as antifoams may be added, even though this is not compulsory.

The granules according to the invention can be prepared by mixing the necessary ingredients and then granulating the mixture by various techniques known per se (granulator, fluidized bed, atomizer, extrusion and the like). This generally ends with crushing followed by screening to the selected particle size within the abovementioned limits. Granules obtained as above and then impregnated with a composition which contains the active material may also be used.

It is preferably obtained by extrusion, the procedure being as indicated in the examples hereinbelow.

EXAMPLE DG1
Dispersible Granules

In a mixer, 90% by weight of active material and 10% of urea beads are mixed. The mixture is subsequently ground in a pin mill. This gives a powder which is moistened with approximately 8% by weight of water. The moist powder is extruded in a perforated-roll extruder. This gives granules which are dried and then crushed and screened to give respectively only those granules which have a size of between 150 and 2000 microns.

EXAMPLE DG2
Dispersible Granules

The following constituents are mixed in a mixer:

| | |
|---|---|
| active material | 75% |
| wetter (sodium alkylnaphthalenesulphonate) | 2% |
| dispersant (sodium polynaphthalenesulphonate) | 8% |
| inert water insoluble filler (kaolin) | 15% |

This mixture is granulated in a fluidized bed in the presence of water and then dried, crushed and screened to give granules of a size between 0.15 and 0.80 mm.

These granules can be used alone, as a solution or as a dispersion in water so as to obtain the desired dose. They can also be used for preparing combinations with other active materials, especially fungicides, the latter being in the form of wettable powders or of granules or aqueous suspensions.

Those compositions which are designed to be suitable for storage and transport contain more advantageously 0.5 to 95% (by weight) of active material.

The invention furthermore relates to a method for the curative or preventative control of crop-phytopathogenic fungi and/or bacteria, characterized in that an effective, non-phytotoxic quantity of a combination of compound A and at least one compound B is applied to the aerial parts of the plants, for example in a fungicidal and/or bactericidal composition according to the invention.

The crop-phytopathogenic fungi which can be controlled by this method are especially the following:

from the group of the Oomycetes:
  those of the genus Phytophthora, such as *Phytophthora phaseoli, Phytophthora citrophthora, Phytophthora capsici, Phytophthora cactorum, Phytophthora palmivora, Phytophthora cinnamoni, Phytophthora megasperma, Phytophthora parasitica, Phytophthora fragariae, Phytophthora cryptogea, Phytophthora porri, Phytophthora nicotianae, Phytophthora infestans* (solanum blight, especially potato or tomato blight);
  from the family of the Peronosporaceae, in particular *Plasmopara viticola* (grapevine downy mildew), *Plasmopara halstedei* (sunflower downy mildew), *Pseudoperonospora* sp. (in particular cucurbit downy mildew (*Pseudoperonospora cubensis*) and hop downy mildew (*Pseudoperonospora humuli*)), *Bremia lactucae* (lettuce downy mildew), *Peronospora tabacinae* (tobacco blue mould), *Peronospora destructor* (onion downy mildew), *Peronospora parasitica* (brassica downy mildew), *Peronospora farinosa* (endive mildew and beet mildew), from the group of the Adelomycetes (ascomycetes):
  those of the genus Alternaria, for example *Alternaria solani* (solanum early blight, especially tomato and potato early blight) *Alternaria porri* (pear tree early blight), *Alternaria mali* (apple tree early blight),
  those of the genus Guignardia, especially *Guignardia bidwellii* (grape black rot),
  those of the genus Venturia, for example *Venturia inaequalis, Venturia pirina* (apple or pear scab),
  those of the genus Oidium, for example vine powdery mildew (*Uncinula necator*); powdery mildew of vegetable crops, for example *Erysiphe polygoni* (powdery mildew of crucifers); *Leveillula taurica, Erysiphe cichoracearum, Sphaerotheca fuligena* (powdery mildew of Cucurbitaceae, of Compositae, of tomato); *Erysiphe conmmunis* (cabbage powdery mildew); *Erysiphe pisi* (powdery mildew of the pea or of the lucerne); *Erysiphe polyphaga* (powdery mildew of the haricot bean and of the cucumber); *Erysiphe unbelliferarum* (powdery mildew of umbellifers in particular of the carrot); *Sphaerotheca humuli* (hop powdery mildew),
  those of the genus Taphrina, for example *Taphrina deformans* (peach leaf curl),
  those of the genus Botrytis cinerea (vine, vegetable and market garden crop, arboriculture, pea, and the like),
  those of the genus *Phomopsis viticola* (vine excoriosis),
  from the group of the Basidiomycetes:
    from the Rhizoctonia spp family, for example *Rhizoctonia solani*.

Diseases of bacterial and viral origin which can be controlled by this method are in particular
  fire blight, *Erwinia amylovora;*
  bacterial spot of stone fruits, *Xanthomonas campestris;*
  pear bacterial canker, *Pseudomonas syringae*.

The crops under consideration for the purposes of the present invention are preferably vegetable crops (beans, onions, cucurbits, cabbage, potatoes, tomatoes, capsicums, spinach, peas, lettuce, celery, endives), fruit crops (strawberry plants, raspberry plants), arboricultural crops (apple trees, pear trees, cherry trees, ginseng, lemon trees, coconut palms, pecan trees, cacao trees, nut trees, hevea trees, olive trees, poplars, banana plants), grapevines, tobacco and ornamentals.

A classification neither by fungi nor by bacteria aimed at, but by target crops, can be illustrated as below:
  grapevine: oidium (*Uncinula necator*), downy mildew (*Plasmopara viticola*), rot (*Botrytis cinerea*), excoriosis (*Phomopsis viticola*) and black rot (*Guignardia bidwellii*),
  Solanaceae: mildew (*Phytophthora infestans*), blight (*Alternaria solani*) and rot (*Botrytis cinerea*),
  vegetable crops: downy mildews (Peronospora Sp., Bremia lactucae, Pseudoperonospora sp.), blight (Alternaria sp.), rot (*Botrytis cinerea*), root rot (Rhizoctonia spp.), oidium (Erysiphe sp.: *Sphaerotheca fulginea*).

arboriculture: scab (*Venturia inaequalis, V. pirina*), bacterial diseases (*Erwinia amiylovora, Xanthomonas campestris, Pseudomonas syringae*), oidium (*Podosphaera leucotricha*) and brown rot (*Monilia fructigena*), botrytis.

citrus fruit: scab (*Elsinoe fawcetti*), melanose (*Phomopsis citri*) and diseases caused by Phytophthora sp.

The fungicidal and/or bactericidal composition of the invention is applied by means of various treatment methods, such as:

spraying a liquid comprising said composition onto the aerial parts of the crops to be treated, dusting, incorporation of granules or powders into the soil, pouring, injection into trees, or painting on.

The preferred treatment method is spraying a liquid onto the aerial parts of the crops to be treated.

"Effective, non-phytotoxic quantity" is to be understood as meaning-such an amount of composition according to the invention to allow fungi and bacteria which are present or likely to appear on the crops to be controlled or destroyed while avoiding any notable symptoms of phytotoxicity on said crops. Such a quantity is likely to vary within wide limits, depending on the fungus or the bacterium to be controlled, the type of crop, the climatic conditions, and the compounds in the fungicidal and/or bactericidal composition according to the invention. This quantity can be determined by systematic field trials known to the skilled worker.

When making use of the method according to the invention, the use concentrations will generally be in this case by foliar treatment on grapevine, vegetable crops, arboriculture, citrus fruit and the like:

25 to 4000 g/ha of compound B, for example pyrimethanil, +150 to 4000 g/ha of compound A and more precisely 50 to 1000 g/ha+250 to 3000 g/ha, that is to say a total dose of composition according to the invention of between 175 to 8000 g/ha, preferably between 300 and 4000 g/ha. 100 to 800 g/ha of compound B and 300 to 900 g/ha of compound A are preferably used, that is to say a total dose of composition according to the invention of between 400 g/ha and 1700 g/ha.

Most advantageously, 501 g/ha of compound A+167 g/ha of compound B (ratio 3/1), that is to say 668 g/ha in total, will be used.

Finally, the invention relates to a product comprising at least one compound A and at least one compound B for controlling phytopathogenic fungi and/or bacteria in an environment by simultaneous, sequential or separate application.

The example which follows is given purely by way of illustrating the invention which is limited thereby in no way whatsoever.

Example: Combination of pyrimethanil and dodine in controlling apple scab

The fungicides evaluated are the following:

| | |
|---|---|
| EXP A: | SC formulation containing 400 g of dodine/l, |
| Scala ® | Sc formulation containing 400 g of pyrimethanil/l. |

The fungicidal compositions evaluated are the following:

| | |
|---|---|
| EXPA at the doses of | 150–300 and 600 g of dodine/ha, |
| Scala ® at the doses of | 50–100 and 200 g of pyrimethanil/ha, |
| EXPA + Scala ® at the does of | 150 + 50 – 300 + 100 and 600 + 200 g of dodine + pyrimethanil/ha. |

Apple plants (var. Melrose Golden) at the 5-6-leaf stage are inoculated with an aqueous suspension containing 150 000 spores of *Venturia inaequalis*/ml of inoculum. The plants are then placed in a climatic cell at 16–18° C., 100% RH (relative humidity) for 3 days. They are then treated with the fungicidal compositions at the doses cited above (12 repeats/dose) in a plant protection mixture at 500 l/ha and are again placed under the conditions described above. One month after the inoculation, scores are awarded. This consists in estimating the diseased leaf surface area in the two leaf stages sensitive to the disease and, by comparing with an untreated contaminated control, in defining the percentage efficacy according to the following formula:

% practical efficacy=100×(% contamination Control–% contamination Trial)/% contamination Control The theoretical efficacy according to the Colby formula is calculated based on the following formula:

% theoretical efficacy A+B=% practical eff. A+% practical eff. B–(% practical eff. A×% practical eff. B/100)

III: Results

| dodine/ pyrimethanil | 0 g/ha | 50 | 100 | 200 |
|---|---|---|---|---|
| | Practical efficacy | | | |
| 0 g/ha | 0 | 65.4 | 65.4 | 61.5 |
| 150 | 30.8 | 84.6 | | |
| 300 | 76.9 | | 92.3 | |
| 600 | 75 | | | 90.4 |
| | Theoretical efficacy (Colby): | | | |
| 0 g/ha | 0 | 65.4 | 65.4 | 61.5 |
| 150 | 30.8 | 76.06 | | |
| 300 | 76.9 | | 92.01 | |
| 600 | 75 | | | 90.38 |
| | Synergism: | | | |
| 0 g/ha | | | | |
| 150 | | 9 | | |
| 300 | | | 0 | |
| 600 | | | | 0 |

Pyrimethanil and dodine offer partial protection when they are used alone. The combination in the ratio dodine/ pyrimethanil=3/1 generates a high level of protection for doses of between 150+50 and 600+200 g/ha.

A certain synergistic relationship is obtained at the 150+ 50 g/ha dose (+9% efficacy).

What is claimed is:

1. A synergistic fungicidal composition comprising, as compound A, dodine and at least one fungicidal compound B selected from the group consisting of cyprodinil, pyrimethanil and mepanipyrim;

said composition comprising the components A and B in a weight ratio A/B of between 1/26 and 160/1.

2. The composition of claim 1, wherein said compound B is pyrimethanil.

3. The composition of claim 1, wherein the ratio A/B is between 1/4 and 60/1.

4. The composition of claim 1, wherein the compounds A and B are mixed with solid or liquid agriculturally acceptable carriers.

5. The composition of claim 1, wherein the amount of compounds A and B are from 0.05 to 95% (by weight).

6. The composition of claim 1, wherein the components A and B have a weight ratio A/B between 3/8 and 9/1.

7. The composition of claim 1, wherein the components A and B have a weight ratio A/B of 3/1.

8. The composition of claim 1, wherein the compounds A and B are mixed with agriculturally acceptable surfactants.

9. A method of controlling phytopathogenic fungi or bacteria in an environment, comprising applying antifungal or antibacterial effective, but non-phytotoxic amount of the composition of claim 1 to said environment.

10. A method for the curative or preventative control of crop-phytopathogenic fungi or bacteria on a plant, comprising applying to the aerial parts of the plant an antifungal or antibacterial effective, but non-phytotoxic quantity of the composition of claim 1.

11. The method of claim 10 wherein the composition of claim 1 is liquid and the application said composition is carried out by spraying.

12. The method of claim 11, wherein said composition has a dose of between 175 and 8000 g/ha and is applied for foliar treatment.

13. The method of claim 12, wherein said composition has a dose of between 400 and 1700 g/ha.

14. The method of claim 12, wherein said composition has a dose of between 300 and 4000 g/ha.

15. The method of claim 13, wherein said composition has a dose of 668 g/ha.

* * * * *